US012708705B2

(12) United States Patent
Robbins et al.

(10) Patent No.: US 12,708,705 B2
(45) Date of Patent: Aug. 18, 2026

(54) NOZZLE, ANAL IRRIGATION SYSTEM, METHODS OF ASSEMBLY AND OF ANAL IRRIGATION

(71) Applicant: CLINISUPPLIES LIMITED, Croxley Park (GB)

(72) Inventors: Paul John Robbins, Norwich Norfolk (GB); Nicholas Ian Harvey, Norwich Norfolk (GB)

(73) Assignee: CLINISUPPLIES LIMITED (GB)

( * ) Notice: Subject to any disclaimer, the term of this patent is extended or adjusted under 35 U.S.C. 154(b) by 895 days.

(21) Appl. No.: 18/013,843

(22) PCT Filed: Jul. 2, 2021

(86) PCT No.: PCT/GB2021/051692
§ 371 (c)(1),
(2) Date: Dec. 29, 2022

(87) PCT Pub. No.: WO2022/003372
PCT Pub. Date: Jan. 6, 2022

(65) Prior Publication Data

US 2023/0277756 A1 Sep. 7, 2023

(30) Foreign Application Priority Data

Jul. 3, 2020 (GB) ..................................... 2010254

(51) Int. Cl.
*A61M 3/02* (2006.01)

(52) U.S. Cl.
CPC ........ *A61M 3/0279* (2013.01); *A61M 3/0291* (2013.01); *A61M 2207/00* (2013.01); *A61M 2207/10* (2013.01); *A61M 2210/1064* (2013.01); *A61M 2210/1067* (2013.01)

(58) Field of Classification Search
CPC .. A61M 3/0279; A61M 3/0291; A61M 3/027; A61M 3/02; A61M 2207/00; A61M 2207/10; A61M 2210/1064; A61M 2210/1067
See application file for complete search history.

(56) References Cited

U.S. PATENT DOCUMENTS 3,916,897 A * 11/1975 Elmore .................. A61F 5/442 604/179
2002/0019613 A1* 2/2002 Alexandersen ..... A61M 3/0241 604/279
2014/0296832 A1* 10/2014 Karmazyn ...... A61M 25/10185 604/514
2020/0178988 A1 6/2020 Henry et al.

FOREIGN PATENT DOCUMENTS

GB 2 565 640 A 2/2019

* cited by examiner

*Primary Examiner* — Tasnim Mehjabin Ahmed
(74) *Attorney, Agent, or Firm* — Thorpe North & Western, LLP.

(57) ABSTRACT

A nozzle suitable for irrigating the rectal and/or bowel cavities, the nozzle comprises an elongate stem incorporating a channel extending there through; whereby fluid may flow, in use, through said channel; said stem incorporating a fluid inlet and one or more fluid outlets; and a first skirt protruding, when secured to said elongate stem, radially from said stem; said first skirt being inherently flexible; whereby said skirt is sufficiently flexible for insertion through the anus and to thereafter rest against the internal wall of the rectum; wherein said first skirt comprises an annular hub which is secured to said elongate stem.

23 Claims, 5 Drawing Sheets

NOZZLE, ANAL IRRIGATION SYSTEM, METHODS OF ASSEMBLY AND OF ANAL IRRIGATION

The present application is a National Stage of International Application No. PCT/GB2021/051692, filed on Jul. 2, 2021, which claims priority to GB Application No. 2010254.7, filed on Jul. 3, 2020, each of which is incorporated herein by reference in its entirety.

TECHNICAL FIELD

The technical field relates to a nozzle for irrigating the rectal and/or bowel cavities and to anal irrigation systems incorporating such nozzles. Further embodiments concern methods of assembly of nozzles and of anal irrigation.

BACKGROUND TO THE INVENTION

The closest prior art known to the applicant is the nozzle described in GB2565640 which was invented by the same inventors. Embodiments of the invention seek to overcome a range of drawbacks identified in their earlier disclosure. Amongst these, the prior art nozzle is only suitable for a particular size of patient and therefore fails to offer the flexibility required in most applications. Furthermore, it required the use of an introducer which held the prior art integrally formed petals in a retracted position during the insertion phase. Embodiments of the invention improve the configuration of the nozzle for improved insertion and therefore does away with any reliance on the inserter. Certain preferred embodiments therefore seek to improve the range of use of the nozzle, to improve the ability to insert the nozzle, and the overall comfort of the patients which rely on the use of the nozzle.

WO2016/007536 is also known to the applicant. It discloses a nozzle for irrigation with an inflatable balloon 38 and therefore doesn't possess a skirt of the kind envisaged in the previously referenced prior art. Inflatable balloons have been found to damage the rectal cavities in certain modes of use. Certain embodiments of the invention overcome these drawbacks whilst providing enhanced flexibility over other prior art embodiments.

WO2018/009871A1 like WO2016/007536 requires an inflatable balloon located between a cuff and the patient-proximal end where the fluid outlets are provided.

SUMMARY OF THE INVENTION

In a first broad independent aspect, an embodiment provides a nozzle suitable for irrigating the rectal and/or bowel cavities, the nozzle comprising an elongate stem incorporating a channel extending there through; whereby fluid may flow, in use, through the channel; the stem incorporating a fluid inlet and one or more fluid outlets; and a first skirt projecting, when secured to the elongate stem, radially from the stem and being provided as the first radially projecting member below said fluid outlets; the first skirt being inherently flexible; whereby the skirt is sufficiently flexible for insertion through the anus and to thereafter rest against the internal wall of the rectum; wherein said first skirt comprises an annular hub; said elongate stem and said first skirt being formed as two separate components; said annular hub being secured to said elongate stem.

This configuration is particularly advantageous as it allows first skirts to be selected with a wide range of outer diameters which may allow the nozzle to be adapted for use with a wider range of individuals dependent upon their size and medical condition. It also improves in certain embodiments not only the flexibility of the attachment but the strength. Furthermore, no inflatable balloon is required and therefore the risk of balloon induced damage is avoided whilst providing the flexibility to adapt to a variety of patient sizes. In preferred embodiments, the first skirt is configured with one or more predetermined cut-outs (eg. radial cut-outs as seen between petals or pre-formed fold lines) to allow the first skirt to collapse on itself when being inserted through the anus.

In a subsidiary aspect, the stem comprises an annular recess which corresponds to the annular hub; whereby the first skirt is secured to the elongate stem. This configuration is particularly advantageous as it provides in certain embodiments the precise location of the attachment and allows for readily securable and durable attachment to be achieved.

In a further subsidiary aspect, the nozzle further incorporates a second skirt projecting radially from the stem; the second skirt being provided in a location which is closer to the fluid inlet than the location of the first skirt; and wherein the elongate stem has a smaller internal diameter in the region of the stem where the annular hub is secured than in the region immediately above the second skirt. This configuration is particularly advantageous as it provides in certain embodiments extra flexibility allowing the lower portion to bend in certain loading directions.

In a further subsidiary aspect, the annular hub is bonded to an outer portion of the stem. This configuration is particularly advantageous as it further improves in certain embodiments the level of security of the attachment.

In a further subsidiary aspect, the elongate stem incorporates a tip which is tapered at its distal extremity and the annular hub has an inner diameter which is lower than the external diameter of the lower part of the tip; the annular hub being sufficiently flexible to flex radially to allow the tip to be pushed through the annular hub and for the annular hub to thereafter flex back into the annular recess to be retained thereby. This configuration is particularly advantageous as it allows in certain embodiments for the first skirt to be secured prior to any additional bonding such as chemical bonding.

In a further subsidiary aspect, the second skirt is less flexible than the first skirt. This allows the advantageous passage of the first skirt through the anus whilst the second skirt would abut against it and remain on the outside.

In a further subsidiary aspect, the second skirt is thicker than the first skirt. This also contributes advantageously to the abutment of the second skirt.

In a further subsidiary aspect, the stem increases in outer diameter towards the second skirt in a region above the second skirt. This provides progressive increase in rigidity towards the second skirt.

In a further subsidiary aspect, the first skirt further incorporates radial slits extending inwardly from its peripheral edge, whereby a plurality of petals are formed. This allows the individual petals to move independently which increases the ease with which the nozzle can be inserted and removed whilst providing support when in place.

In a further subsidiary aspect, the first skirt comprises five or fewer than five petals. This configuration is particularly advantageous for its ease of passage whilst reducing the requirements for slits.

In a further subsidiary aspect, the first skirt has an outer diameter which is greater than the outer diameter of the second skirt. This is particularly advantageous when adapting the nozzle for use with patients where larger diameters are required.

In a further subsidiary aspect, the first skirt comprises no fold lines. This configuration is an advantageous simplification over the prior art nozzle as no fold lines are required whilst the performance of the nozzle is improved, in certain embodiments.

In a further subsidiary aspect, the elongate stem incorporates a tip and at least one of the fluid outlets is formed as a first aperture in the tip.

In a further subsidiary aspect, the tip comprises a side wall, wherein the side wall further incorporates at least a fluid outlet. This provides an improvement in terms of pressure balance between the various apertures.

In a further subsidiary aspect, the side wall incorporates a further fluid outlet. This further improves the fluid dynamics in certain embodiments.

In a further subsidiary aspect, the further fluid outlet is located diametrically opposite a fluid outlet. This configuration is particularly advantageous in terms of minimising in certain embodiments blockages and the like.

In a further subsidiary aspect, the fluid outlet has a distal lip which is rounded. This configuration is particularly advantageous as it minimises in certain embodiments the presence of any sharp edges thus minimising the risk of inadvertent injury to a patient.

In a further subsidiary aspect, the annular hub comprises a first outer diameter located above the first skirt and a second outer diameter located below the first skirt; the first outer diameter above the first skirt being smaller than the second outer diameter. This configuration provides improved support for the first skirt.

In a further broad independent aspect, an embodiment concerns an anal irrigation system comprising a nozzle in accordance with any one of the preceding aspects.

In a further subsidiary aspect, the system further comprises a plurality of first skirts with two or more different outer diameters; wherein each one of the skirts comprises an annular hub shaped and configured to be secured to the stem. This allows the system to have greater flexibility and to be readily adapted for use with a wider range of patients.

In a further broad independent aspect, an embodiment provides a method of assembling a nozzle suitable for irrigating the rectal and/or bowel cavities comprising the steps of:

providing an elongate stem incorporating a channel extending there through; whereby fluid may flow, in use, through the channel; the stem incorporating a fluid inlet and one or more fluid outlets;

selecting a first skirt with an annular hub; and securing the annular hub to the stem.

In a further subsidiary aspect, the method of assembling a nozzle comprises the step of providing a stem with an annular recess and placing said annular hub in the annular recess.

In a further subsidiary aspect, the method of assembling a nozzle comprises the step of bonding the annular hub to the stem.

In a further subsidiary aspect, the method of assembling an anal irrigation system comprising the steps of assembling a nozzle according to any one of the preceding aspects, and further providing a plurality of tubular sections, a plurality of connectors suitable for connecting a plurality of tubular sections, and a pump for pressurising the liquid of the irrigation system, and connecting the nozzle, the tube sections and a pump.

In a further broad independent aspect, the method of anal irrigation comprises the steps of at least partially inserting a nozzle in accordance with any of the preceding aspects in a patient in need of anal irrigation.

In a subsidiary aspect, the method of anal irrigation comprises the step of selecting a nozzle with a first skirt from a group of nozzles with first skirts of different outer diameters.

In a further broad independent aspect, an embodiment provides a nozzle suitable for irrigating the rectal and/or bowel cavities, the nozzle comprising an elongate stem incorporating a channel extending there through; whereby fluid may flow, in use, through the channel; the stem incorporating a fluid inlet and one or more fluid outlets; and a first skirt projecting, when secured to the elongate stem, radially from the stem; the first skirt being inherently flexible; whereby the skirt is sufficiently flexible for insertion through the anus and to thereafter rest against the internal wall of the rectum;

wherein the nozzle further incorporates a second skirt projecting radially from the stem; the second skirt being provided in a location which is closer to the fluid inlet than the location of the first skirt; and wherein the elongate stem has a smaller internal diameter in the region of the stem where the first skirt is secured than in the region immediately above the second skirt.

In a further broad independent aspect, an embodiment provides a nozzle suitable for irrigating the rectal and/or bowel cavities, the nozzle comprising an elongate stem incorporating a channel extending there through; whereby fluid may flow, in use, through the channel; the stem incorporating a fluid inlet and one or more fluid outlets; and a first skirt projecting, when secured to the elongate stem, radially from the stem; the first skirt being inherently flexible; whereby the skirt is sufficiently flexible for insertion through the anus and to thereafter rest against the internal wall of the rectum; wherein the first skirt comprises five or fewer than five petals.

In a further broad independent aspect, an embodiment provides a nozzle suitable for irrigating the rectal and/or bowel cavities, the nozzle comprising an elongate stem incorporating a channel extending there through; whereby fluid may flow, in use, through the channel; the stem incorporating a fluid inlet and one or more fluid outlets; and a first skirt projecting, when secured to the elongate stem, radially from the stem; the first skirt being inherently flexible; whereby the skirt is sufficiently flexible for insertion through the anus and to thereafter rest against the internal wall of the rectum; wherein the nozzle further incorporates a second skirt projecting radially from the stem; the second skirt being provided in a location which is closer to the fluid inlet than the location of the first skirt; wherein the first skirt has an outer diameter which is greater than the outer diameter of the second skirt.

BRIEF DESCRIPTION OF THE DRAWINGS

The invention will now be described with reference to the accompanying drawings which show by way of example only, embodiments of an apparatus for facilitating irrigation of the rectum and/or the bowel and/or the colon cavities via the anus. In the drawings.

DETAILED DESCRIPTION OF THE EMBODIMENTS

Figure 1:
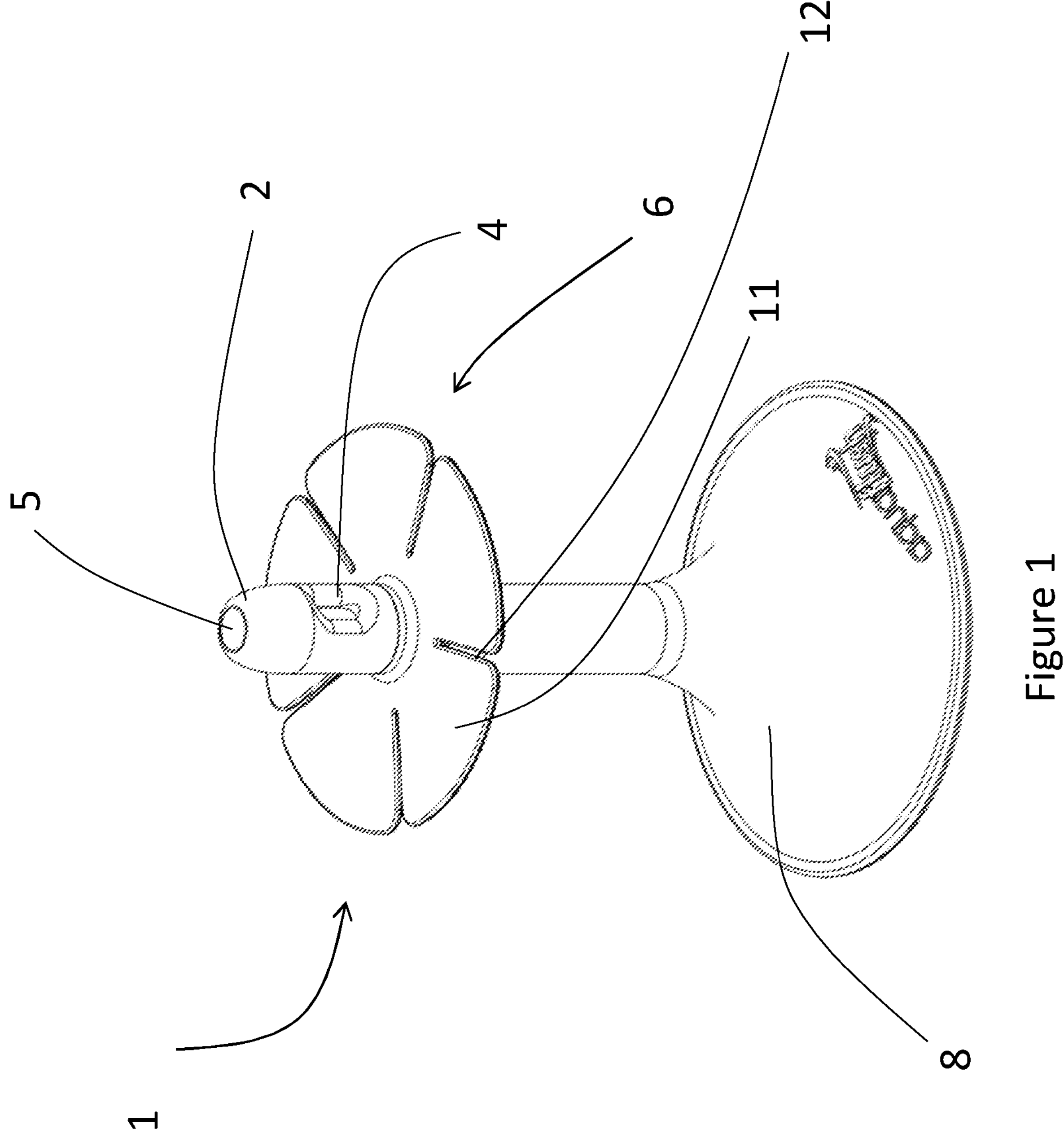
FIG. 1 is a perspective view of an anal irrigation nozzle in multiple views.
Figure 2:
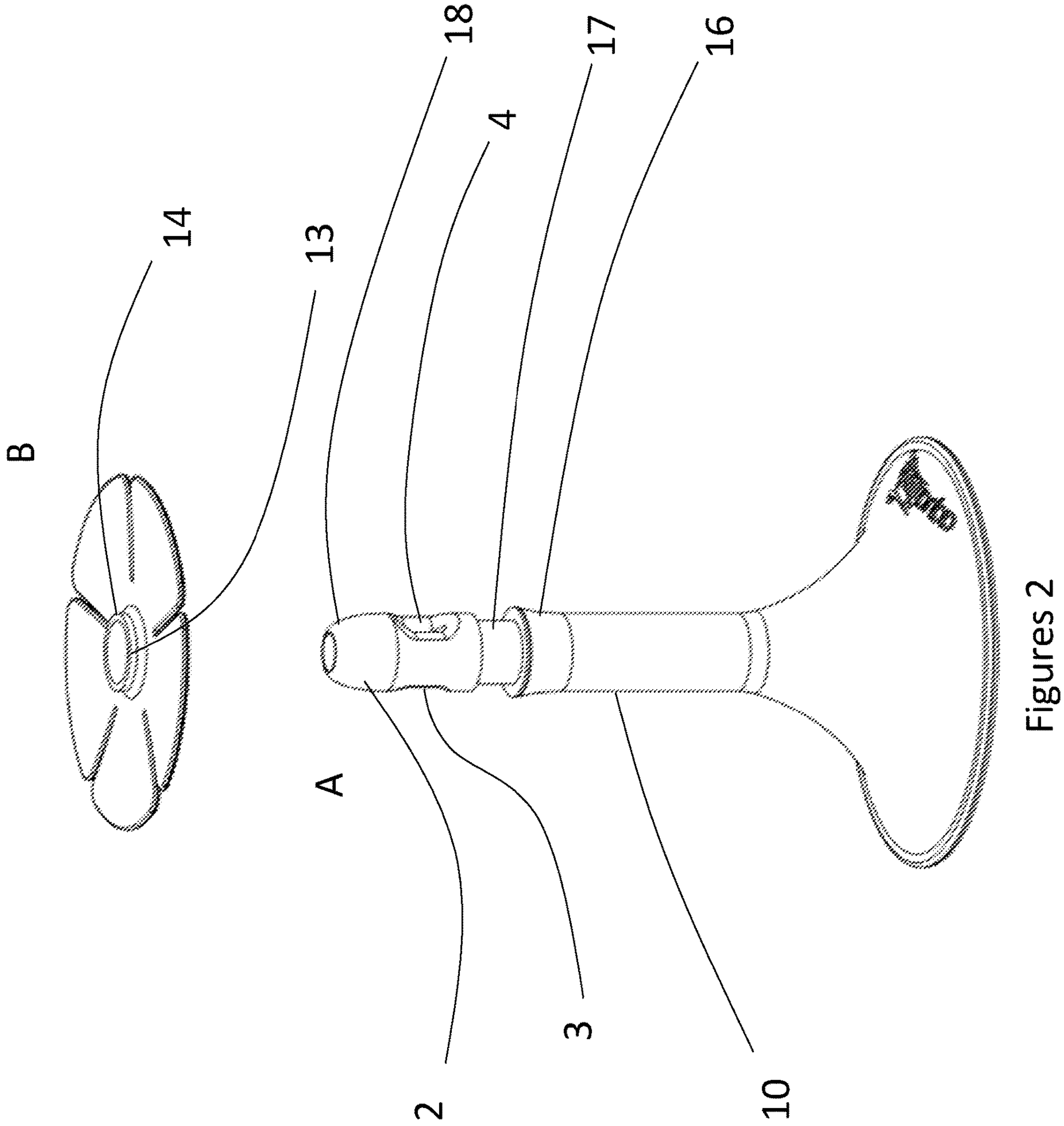
FIG. 2A shows the stem of an anal irrigation nozzle in side elevation.
FIG. 2B shows in perspective view a first skirt suitable for attachment to an anal irrigation nozzle.
Figure 3:
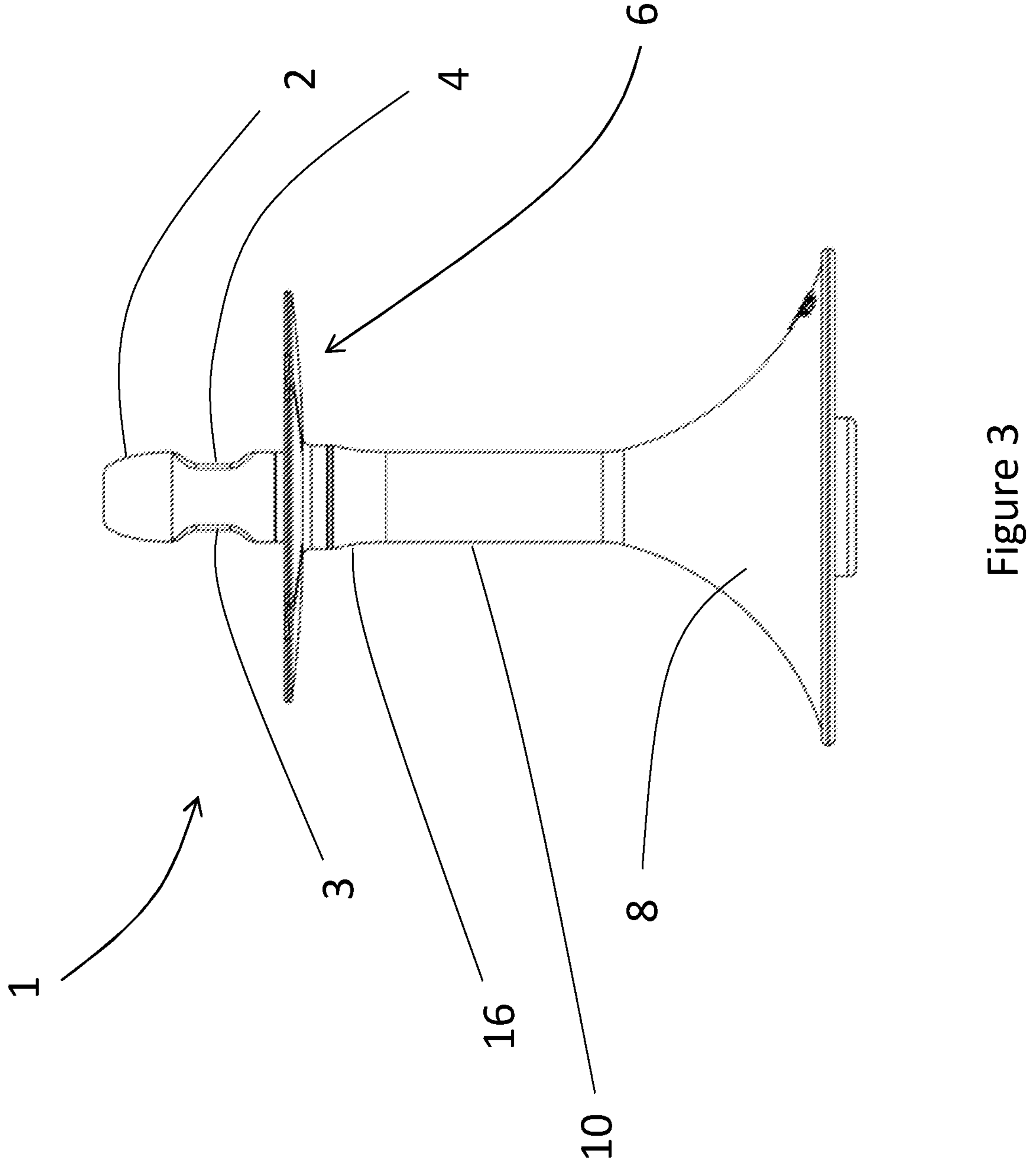
FIG. 3 shows a side elevation of the anal irrigation nozzle in accordance with an embodiment of the invention.
Figure 4:
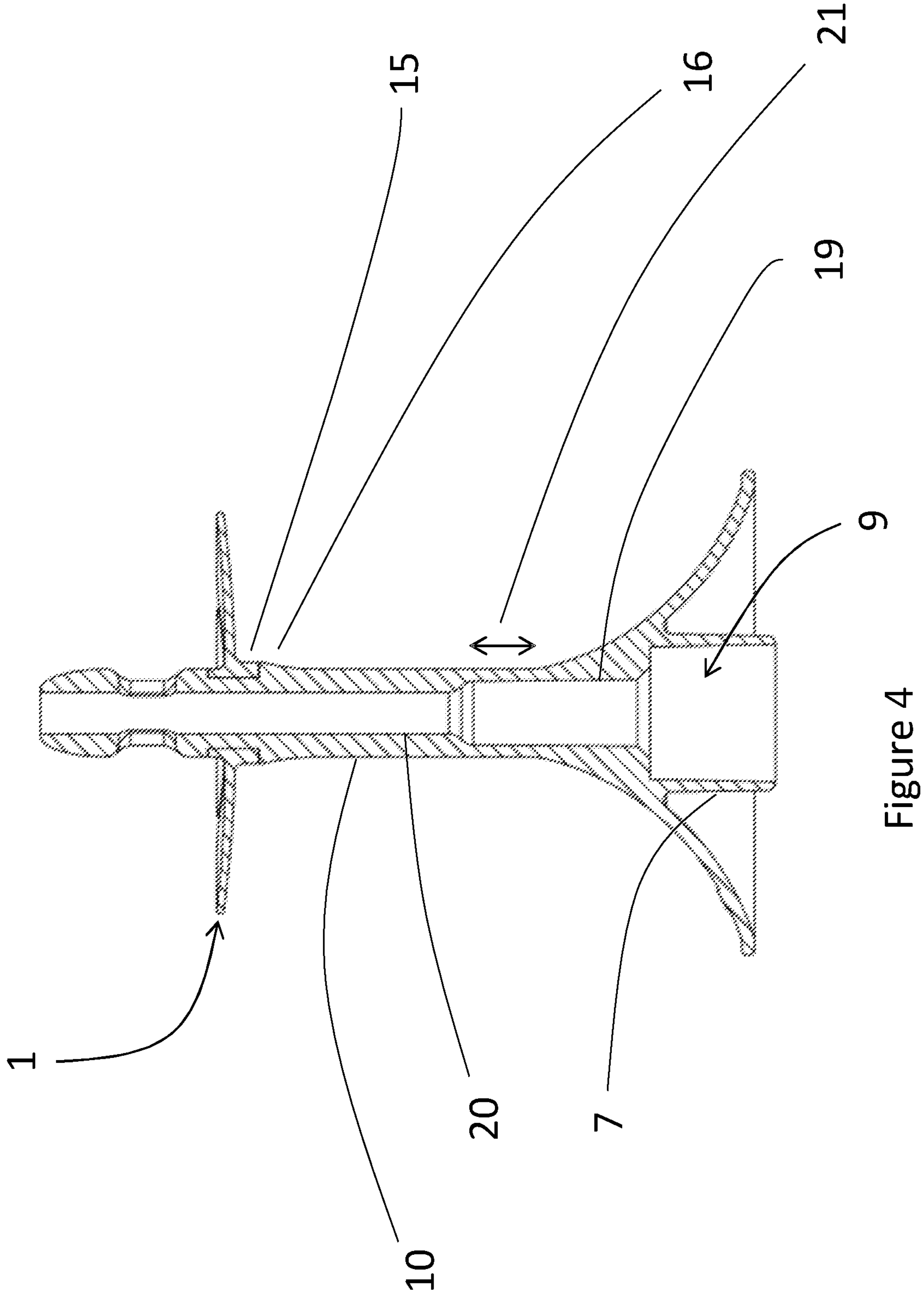
FIG. 4 shows a cross-sectional view from the nozzle.
Figure 5:
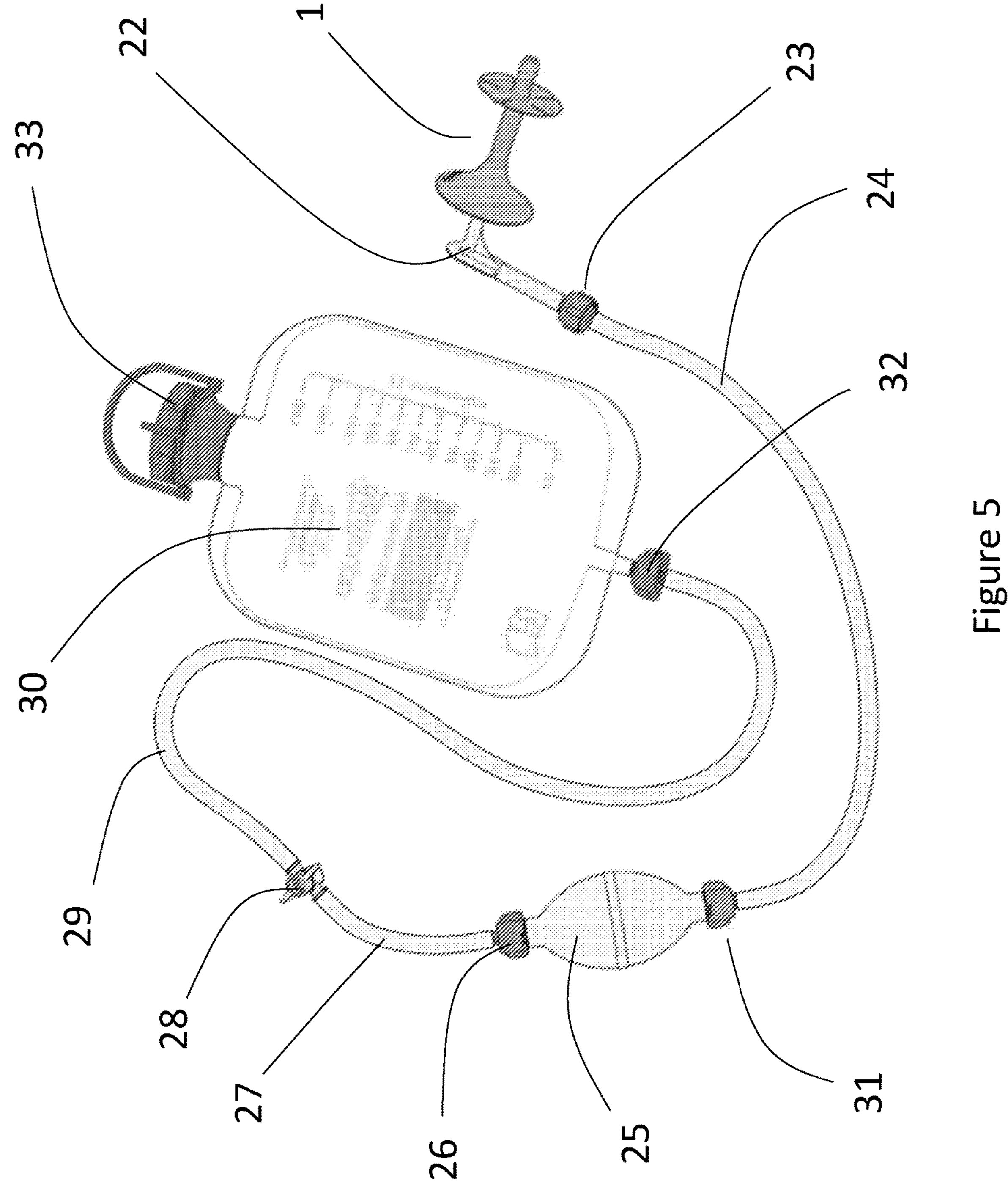
FIG. 5 shows an assembly of an anal irrigation system.

In an embodiment, the invention provides a nozzle attachment designed and configured to be used in conjunction with a tube configuration, for use as part of an anal irrigation apparatus or an anal irrigation system which may be of the kind shown in FIG. 5. The primary function of the nozzle is to allow the introduction of fluid into a patient's bowel to initiate an irrigation session. The nozzle is designed to create an improved insert and location of the nozzle in the rectum of the patient to prevent premature and unwanted leakage of fluid and fecal matter from the anus during an irrigation session. Nozzle 1 comprises a superior tip 2 incorporating one or more holes referenced respectively 3 (see FIG. 2), 4 and 5 and a first radially extending flexible skirt 6, a connector 7 (see FIG. 4) incorporating a second radially extending skirt 8 and an aperture 9 suitable for attachment to a tube and a flexible stem connecting therebetween. In use, the tip 2 is designed to be inserted in the anus, the first skirt 6 capable of deforming such that it is suitable for insertion passed the anus of a patient. The second skirt 8 on the connector is less flexible and is shaped to resist entry into the anus, preventing the nozzle from being fully inserted within the anus and optimally locating the nozzle such that the first skirt sits potentially across the anus and the flexible stem 10 sits within the rectum. The flexible first skirt 6 is resilient, and after deformation for insertion into the anus, returns to its original shape. At the conclusion of the irrigation session, the first skirt 6 can deform in the opposite direction as for insertion, allowing the nozzle to be removed from the patient's rectum and the fluid and fecal matter to drain away.

Although the current embodiment, describes the use of the nozzle as a separate attachment for use with a tube, further embodiments provide a nozzle which is integral with a tube or pump apparatus.

Furthermore, embodiments are envisaged where the nozzle is integral with an anal irrigation system such as for example in FIG. 5. It should be understood that the invention is particularly advantageous when optionally associated with mechanical, self-controlled systems or automated pump systems. The nozzle itself may be optionally a one-use disposable nozzle. In further embodiments, a lubricant may be employed either with the nozzle or the outer surface of the nozzle may have a particularly low level of friction or even an integral lubricated surface to allow the nozzle to be ready for use.

To provide clarity, the elements of an embodiment of the invention which are common to each figure have retained identical numerical references throughout.

First skirt 6 comprises 5 petals such as petal 11 separated by a number of radially extending slits such as slit 12. The slits are generally oblong in shape with a radius in their region most proximal to the stem. Adjacent outer most edges of the petals are also rounded. The slits do not extend up to the stem and commence at a distance which is at least ⅙ of their length whereby a web is provided between the slits and the stem.

An annular hub 13 (see FIG. 2B) is provided which defines a hole through which the nozzle's stem may be inserted. The annular hub is generally cylindrical and may comprise an inner diameter which may remain constant along its length. Its external diameter however has at least several diameters. The upper external diameter 14 located above the first skirt has a smaller external diameter than the lower external diameter 15 located below the skirt (see FIG. 4). In other words, the upper portion of the annular hub is not as thick as the lower portion of the annular hub. This provides greater support under the skirt.

In a preferred embodiment, stem 10 tapers outwards towards the lower diameter 15 as shown in region 16 which provides a wider support surface against which the annular hub may rest once fitted onto the stem. In preferred embodiments, the annular hub 13 corresponds precisely in shape and configuration to the annular recess 17. The annular hub may preferably be of inherently elastic material in order to allow it to stretch when the tip 2 of the stem is forced into the hole defined by the annular hub. In order to facilitate the insertion of the tip into the annular hub, the tip may have a distal region 18 which reduces in diameter towards its extremity and is thus rounded or tapered. The presence of the distal hole and the side holes 3 and 4 also facilitate the ability to momentarily reduce the diameter of the stem to allow the passage of the upper portion of the tip through the annular hub. Once the stem is sufficiently inserted into the annular hub so that the annular hub flexes back into the annular recess of corresponding size, the annular hub is effectively secured in place without necessarily requiring any additional bonding of the two separate components of the nozzle. In preferred embodiments, the annular hub may be further secured to the stem by the application of an appropriate adhesive or by other bonding mechanism which may for example lead to the components being chemically bonded.

Whilst the preceding embodiment envisages the use of a particular size of first skirt, other embodiments envisage first skirts which may be of greater outer diameter in order to be suitable for use with particular patients depending on their specific requirements.

As shown in FIG. 4, the inner diameter 19 of the stem is greater in the region of the second skirt 8 than it is either side of the annular recess as shown by inner diameter 20. This leads in combination with the reduction in external diameter above the second skirt to a region 21 where the thickness of the stem's wall is reduced, depending on the loads applied to the nozzle, to a region where the stem could more readily bend. This region of reduced wall thickness is also advantageous as it may also allow an operator to see or feel the extremity of a tubular if inserted into said portion.

FIG. 5 shows an assembled anal irrigation system comprising a nozzle 1 of the kind described above which is secured to tubular portion 22 which is inserted into aperture 9 of the nozzle and into the inner diameter 19 in order to achieve a sufficiently watertight fit. Tubular portion 22 has a bend forming a substantially right angle and is in turn connected via a connector 23 to flexible tubular 24. A further connector 31 attaches tubular 24 to a manually operable pump or chamber 25 which possesses flexible walls. Pump 25 is in turn attached via connector 26 to a tubular 27 which engages with a receiving portion of a valve 28. Thereafter, a further tubular 29 extends between valve 28 and the connector 32 for securing to a pouch 30. The pouch comprises a filling inlet 33 and an eye for facilitating the attachment of the pouch to any appropriate securing means such as a hook.

The invention claimed is:

1. A nozzle suitable for irrigating the rectal and/or bowel cavities, the nozzle comprising: an elongate stem incorporating a channel extending there through; whereby fluid may flow, in use, through the channel; said elongate stem incorporating a fluid inlet and at least one fluid outlet; and a first skirt projecting, when secured to said elongate stem, radially from said elongate stem and being provided as the first radially projecting member below said at least one fluid outlet; said first skirt being inherently flexible; whereby said first skirt is sufficiently flexible for insertion through the anus and to thereafter rest against the internal wall of the rectum; wherein said first skirt comprises an annular hub; said elongate stem and said first skirt being formed as two separate components; wherein said elongate stem comprises an annular recess which corresponds to said annular hub; and wherein said elongate stem incorporates a tip which is tapered at its distal extremity and said annular hub has an inner diameter which is lower than the external diameter of the lower part of said tip; said annular hub being sufficiently flexible to flex radially to allow the tip to be pushed through said annular hub and for the annular hub to thereafter flex back into said annular recess to be retained thereby.

2. The nozzle according to claim 1, wherein said nozzle further incorporates a second skirt projecting radially from said elongate stem; said second skirt being provided in a location which is closer to the fluid inlet than the location of the first skirt; and wherein said elongate stem has a smaller internal diameter in the region of the elongate stem where said annular hub is secured than in the region immediately above said second skirt.

3. The nozzle according to claim 2, wherein said second skirt is less flexible than said first skirt.

4. The nozzle according to claim 2, wherein said second skirt is thicker than said first skirt.

5. The nozzle according to claim 2, wherein said elongate stem increases in outer diameter towards said second skirt in a region above said second skirt.

6. The nozzle according to claim 2, wherein said first skirt has an outer diameter which is greater than the outer diameter of said second skirt.

7. The nozzle according to claim 1, wherein said annular hub is bonded to an outer portion of said elongate stem.

8. The nozzle according to claim 1, wherein said first skirt further incorporates radial slits extending inwardly from its peripheral edge, whereby a plurality of petals are formed.

9. The nozzle according to claim 8, wherein said first skirt comprises five or fewer than five petals.

10. The nozzle according to claim 1, wherein said first skirt comprises no fold lines.

11. The nozzle according to claim 1, wherein said elongate stem incorporates a tip and at least one of said fluid outlets is formed as a first aperture in said tip.

12. The nozzle according to claim 11, wherein said tip comprises a side wall, wherein said side wall further incorporates at least a fluid outlet.

13. The nozzle according to claim 12, wherein said side wall incorporates a further fluid outlet.

14. The nozzle according to claim 13, wherein said further fluid outlet is located diametrically opposite the fluid outlet.

15. The nozzle according to claim 11, wherein said fluid outlet has a distal lip which is rounded.

16. The nozzle according to claim 1, wherein said annular hub comprises a first outer diameter located above said first skirt and a second outer diameter located below said first skirt; the first outer diameter above said first skirt being smaller than said second outer diameter.

17. An anal irrigation system comprising a nozzle in accordance with claim 1.

18. The anal irrigation system according to claim 17, further comprising a plurality of first skirts with two or more different outer diameters; wherein each one of said skirts comprises an annular hub shaped and configured to be secured to said stem.

19. A method of anal irrigation comprises the steps of at least partially inserting a nozzle in accordance with claim 1 in a patient in need of anal irrigation.

20. A method of assembling a nozzle suitable for irrigating the rectal and/or bowel cavities comprising the steps of:

providing an elongate stem that incorporates an annular recess and a tip which is tapered at its distal extremity, said stem further incorporating a channel extending there through; whereby fluid may flow, in use, through said channel, and said stem incorporating a fluid inlet and one or more fluid outlets;

selecting a first skirt with an annular hub that is sufficiently flexible; and securing said annular hub to said stem by pushing the tapered tip through the annular hub, causing the annular hub to flex radially, and allowing the annular hub to thereafter flex back into the annular recess to be retained thereby; wherein said first skirt projects radially and is the first radially projecting member of the nozzle below said fluid outlets.

21. The method of assembling a nozzle according to claim 20, wherein the step of securing includes placing said annular hub in said annular recess on the stem.

22. The method of assembling a nozzle according to claim 20, comprising the step of bonding said annular hub to said stem.

23. A method of assembling an anal irrigation system comprising the steps of assembling a nozzle according to claim 20, and further providing a plurality of tubular sections, a plurality of connectors suitable for connecting a plurality of tubular sections, and a pump for pressurising the liquid of the irrigation system, and connecting said nozzle, said tube sections and a pump.

* * * * *